(12) United States Patent
Wieraszko et al.

(10) Patent No.: US 8,932,195 B2
(45) Date of Patent: Jan. 13, 2015

(54) PROCESS AND APPARATUS FOR IMPROVING NEURONAL PERFORMANCE

(75) Inventors: Andrzej Wieraszko, Princeton, NJ (US); Zaghloul Ahmed, Staten Island, NY (US)

(73) Assignee: Research Foundation of the City University of New York, New York, NY (US)

( * ) Notice: Subject to any disclaimer, the term of this patent is extended or adjusted under 35 U.S.C. 154(b) by 1739 days.

(21) Appl. No.: 11/768,703

(22) Filed: Jun. 26, 2007

(65) Prior Publication Data

US 2008/0004484 A1     Jan. 3, 2008

Related U.S. Application Data

(60) Provisional application No. 60/817,935, filed on Jun. 30, 2006.

(51) Int. Cl.
    *A61N 2/04*             (2006.01)
    *A61N 2/02*             (2006.01)

(52) U.S. Cl.
    CPC ............................. *A61N 2/02* (2013.01)
    USPC ..................................................... 600/9

(58) Field of Classification Search
    USPC ........................ 600/9–15; 607/2, 62
    See application file for complete search history.

(56) References Cited

U.S. PATENT DOCUMENTS

| | | | |
|---|---|---|---|
| 5,047,005 A | | 9/1991 | Cadwell |
| 5,100,373 A | * | 3/1992 | Liboff et al. ............ 600/13 |
| 5,224,922 A | * | 7/1993 | Kurtz ................... 600/13 |
| 5,450,859 A | * | 9/1995 | Litovitz ................. 128/897 |
| 5,562,718 A | | 10/1996 | Palermo |
| 5,738,625 A | * | 4/1998 | Gluck ..................... 600/9 |
| 7,160,241 B1 | * | 1/2007 | Herbst .................. 600/13 |
| 7,758,490 B2 | * | 7/2010 | Pilla et al. .............. 600/13 |
| 2002/0161415 A1 | | 10/2002 | Cohen et al. |
| 2003/0171640 A1 | * | 9/2003 | Canedo .................... 600/9 |
| 2003/0217754 A1 | * | 11/2003 | Thomas et al. ........... 128/856 |
| 2004/0172097 A1 | | 9/2004 | Brodard et al. |
| 2006/0052657 A9 | | 3/2006 | Zabara |

(Continued)

FOREIGN PATENT DOCUMENTS

| | | |
|---|---|---|
| WO | 2011050255 A2 | 4/2011 |
| WO | 2011119251 A2 | 9/2011 |

OTHER PUBLICATIONS

Laycock, D.C., Pulse Magnetic Field Therapy and the Physiotherapist, http://www.tgselectronics.com.au/physio.html, Jul. 1997.

(Continued)

*Primary Examiner* — Christine Matthews
(74) *Attorney, Agent, or Firm* — Burns & Levinson LLP; Jacob N. Erlich; Orlando Lopez

(57) ABSTRACT

A method for improving neuronal performance of a target nerve of a patient according to one exemplary embodiment includes the step of: exposing the nerve to a pulsed magnetic field generated by DC current having a predetermined magnetic field strength at a predetermined frequency. The predetermined magnetic field strength and the predetermined frequency are selected such that an amplitude of a compound action potential of the target nerve increases as a result of the exposure and remains elevated for a time period after the exposure has ended.

43 Claims, 7 Drawing Sheets

(56) References Cited

U.S. PATENT DOCUMENTS

2006/0116720 A1    6/2006    Knoblich
2008/0208287 A1    8/2008    Palermo et al.
2009/0204175 A1    8/2009    Zanella et al.

OTHER PUBLICATIONS

Agrawal, Sandeep K., et al., Mechanisms of Secondary Injury to Spinal Cord Axons In Vitro: Rols of $Na^+$, $Na^+$-K-ATPase, the $Na^+$-$H^+$ Exchanger, and the $Na^+=Ca^{2+}$ Exchanger, The Journal of Neuroscience, 16(2):545-552, 1996.

Wieraszko, A., Dantrolene Modulates the Influence of Steady Magnetic Fields on Hippocampal Evoked Potentials In Vitro, Bioelectromagnetics 21:175-182 (2000).

International Search Report of the International Searching Authority, International Application No. PCT/US2010/053720, filed on Oct. 22, 2010.

International Application Serial No. PCT/US2010/053720, filed on Oct. 22, 2010, in its entirety.

International Search Report of the International Searching Authority, International Application No. PCT/US2011/022283, filed on Jan. 24, 2011.

International Application No. PCT/US2011/022283, filed on Jan. 24, 2011, in its entirety.

* cited by examiner

PROCESS AND APPARATUS FOR IMPROVING NEURONAL PERFORMANCE

CROSS-REFERENCE TO RELATED APPLICATION

The present application claims the benefit of U.S. patent application Ser. No. 60/817,935, filed Jun. 30, 2006, which is hereby incorporated by reference in its entirety.

TECHNICAL FIELD

The present invention relates to pulsed magnetic fields, the nervous system, and to improvements in neuronal performance. More specifically, the invention is directed towards a method and an apparatus for improving neuronal performance by exposure to a pulsed magnetic field (PMF).

BACKGROUND

The nervous system is an integral part of the human body and its major function is to react to the external environment and to coordinate the function of the different parts of the body accordingly. The whole nervous system is divided into peripheral and central nervous systems. Although their physiological role is similar, there are significant differences in their functions. Nerves are responsible for transmitting electrical signals throughout the body to stimulate muscles and regulate the activity of vital organs. The central nervous system, which consists mainly of the brain and spinal cord, is responsible for creating electrical signals which are then sent throughout the body to initiate a response in an innervated organ or limb. The major function of the peripheral nervous system is to stimulate and initiate the contraction of the muscles which move different parts of the human body (mainly arms and legs), and regulate the activity of the internal organs. The nerves of the peripheral nervous system originate in the spinal cord and through long processes called axons innervate distant body parts. The message travels along the axon in the form of an electrical signal, called compound action potential (CAP). Thus, the peripheral nervous system consists of the different nerves through which the electrical signals travel throughout the body and electrical signals are transmitted from one nerve to another through axons, fiber-like extensions from a nerve cell.

An electrical signal traveling through a nerve is called an action potential. This potential is quantifiable and can be expressed in terms of voltage. This potential is responsible for initiating a response in an organ or limb. The strength of the compound action potential (the sum of the action potentials generate by several axons) correlates to the strength of the response. For example, if the compound action potential is sent through a peripheral nerve to initiate the contraction of a muscle, the stronger the compound action potential, the faster and/or stronger the muscle contraction will be.

Any impairment or inhibition in the transmission of the compound action potential can result in a weaker response from the innervated organ. Impairment of the compound action potential transmission could even result in paralysis of the skeletal muscles, i.e., the impairment causes the compound action potential to be too weak to initiate any response in the skeletal muscles, and thus, the patient is unable to move the limb, etc. There are various diseases and conditions in which the transmission of the compound action potential is impaired. Neuropathies such as distal axonopathies, myelinopathies, neuronopathies and autonomic neuropathies are all characterized by a significant reduction in the ability of the nerves to generate and transmit an action potential. Hyporeflexia and areflexia, characterized by weak or absent reflexes, are often linked to diminished compound action potential transmission. The symptoms of these diseases and conditions may be alleviated and the functioning of the innervated organs can be improved with a treatment that facilitates the transmission of the compound action potential.

As mentioned above, the role of the spinal cord, which is a part of the central nervous system, is to transmit the information between the brain and the peripheral nervous system. Any damage to the spinal cord may have devastating effects on the performance of the vital body function. The brain, besides controlling the activity of the spinal cord and peripheral nervous system, is responsible for learning and memory and for utilizing acquired information to improve survival skills.

Even a person without such a disease or condition could benefit from a treatment that facilitates compound action potential transmission. Such a treatment could enhance the performance of an innervated organ, enhancing the person's performance of an activity that utilizes the innervate organ. Furthermore, the treatment may be used to alleviate pain associated with a muscle, or to simply provide a person with a healthier feeling in that muscle.

Magnetic fields have been used in treatments for reducing pain, facilitation of bone healing and to promote overall muscle activity. The effect of a steady magnetic field on the compound action potential of sensory nerves have been described in McLean et al. "Effects of steady magnetic fields on action potentials of sensory neurons in vitro", available at http://www.holcombhealthcare.com/reports/pub-effect.h-tml, which is hereby incorporated by reference. The effects of a steady magnetic field on neuronal performance are not significant, and they are not sustained once the magnetic field is removed. Furthermore, there is some evidence that suggests that the body adapts to the steady magnetic field after a certain amount of time, and therefore exposure to that field will have no affect on neuronal performance.

Pulsed magnetic fields (PMF), i.e., magnetic fields in which the field strength is regularly alternated between different field strengths, have also been used in various treatments. Laycock, et al. "Pulsed magnetic field therapy and the physiotherapist", available at http://www.tgselectronics.com.au/physio.html, which is hereby incorporated by reference, discusses using a PMF to resolve soft tissue injuries, facilitate bone fractures and reduce pain. Laycock describes that a "magnetic field pulsed at 5 Hz with a base frequency of 50 Hz" was as useful as an icepack in dispersing bruises and that a magnetic field having "a base frequency of 200 Hz pulsed at between 5 and 25 pulses per second" was most effective in reducing pain. The PMF used in such treatments is the result of using a magnetic field generating element with an AC power source. As the AC current alternates between its maximum positive and negative flows, the magnetic field pulsates between its maximum field strengths in both polarities, creating a saw-tooth like shaped magnetic field wave form, such as that shown in FIG. 1a. The magnetic field described in Laycock is one in which the saw-tooth like base magnetic field is alternately turned on and off at a given frequency, such as that shown in FIG. 1b. These treatments, however, do not produce significant improvements in neuronal performance.

It would therefore be desirable and advantageous to provide method and an apparatus of improving neuronal performance by facilitating the transmission of the compound action potential by exposure to a magnetic field that overcomes the disadvantages of the prior art, while at the same time improves neuronal performance.

SUMMARY

A method for improving neuronal performance of a target nerve of a patient according to one exemplary embodiment includes the step of: exposing the nerve to a pulsed magnetic field generated by DC current having a predetermined magnetic field strength at a predetermined frequency. The predetermined magnetic field strength and the predetermined frequency are selected such that an amplitude of a compound action potential of the target nerve increases as a result of the exposure and remains elevated for a time period after the exposure has ended.

An apparatus for improving neuronal performance of a target nerve of a patient, according to one exemplary embodiment includes a body for placement proximate to the target nerve, with the body having at least one magnetic field generation element that receives DC current and generates a pulsed magnetic field having a predetermined magnetic field strength at a predetermined frequency. The predetermined magnetic field strength and the predetermined frequency are selected such that an amplitude of the compound action potential of the target nerve increases as a result of exposure to the pulsed magnetic field and remains elevated for a time period after the exposure has ended.

The method and apparatus of the present invention are useful in a treatment to enhance neuronal performance. The present treatment is useful for people suffering from a disease or condition in which the transmission of the compound action potential is impaired. Examples of such diseases and conditions are neuropathies, such as, distal axonopathies, myelinopathies, neuronopathies and autonomic neuropathies and hyporeflexia and areflexia. This treatment is even useful in the regeneration of muscles or organs that have been considered paralyzed due to severe impairment of the compound action potential transmission. The present treatment is also useful in enhancing the neuronal performance of an animal not suffering from any such disease or condition. Such a person could enhance the performance of a particular organ or muscle by enhancing the neuronal performance of that organ or limb. This treatment is also useful in relieving pain or to simply provide a person with a healthier feeling in a particular muscle or organ.

BRIEF DESCRIPTION OF THE FIGURES

These and other objects and features of the invention will become more apparent by referring to the drawings, in which.

DETAILED DESCRIPTION OF THE INVENTION

Figure 1A:
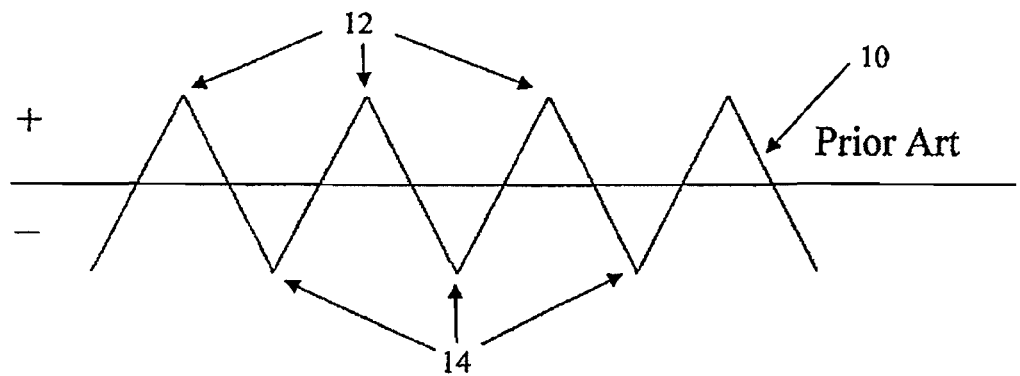
FIG. 1a is a schematic illustrating a wave form of a conventional pulsed magnetic field (PMF)

According to one aspect of the present invention, neuronal performance can be improved by exposing target neurons to a pulsed magnetic field (PMF) generated by DC current. This is in contrast to conventional PMF type devices and applications where the pulsed magnetic field is generated by AC current. This causes the magnetic field strength to constantly change, alternating between maximum values in both polarities. FIG. 1a illustrates a wave form 10 of a conventional pulsed magnetic field (PMF). The wave form 10 shows that the magnetic field strength is constantly changing, alternating between maximum points 12 in the positive polarity (maximum positive values) and maximum points 14 in the negative polarity (maximum negative values).

Figure 1B:
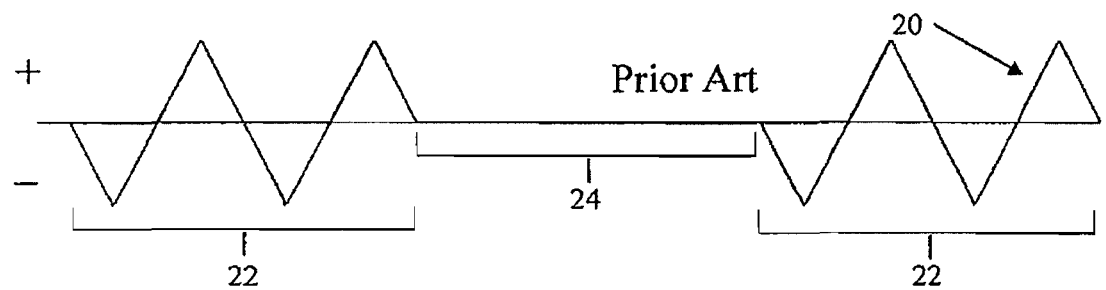
FIG. 1b is a schematic illustrating a wave form of a conventional PMF with a base frequency.

A PMF with a base frequency, as described by the previously mentioned Laycock reference, is in the form of a PMF that is alternately turned on and off so as to produce the wave form 20 illustrated in FIG. 1b. Segments 22 of the wave form 20 show that when the PMF is activated, the magnetic field strength alternates between maximum values in both polarities similar to FIG. 1a. Segment 24 of the wave form shows that when the PMF is not activated, the magnetic field strength remains zero.

Accordingly, in either of the PMF arrangements of FIGS. 1a and 1b, the magnetic strength alternates between maximum values in both polarities.

Unlike conventional PMF devices and applications, such as those in FIGS. 1a and 1b, a method of treatment and related apparatuses (medical or therapeutic instruments) according to the present invention is based on a PMF that is generated by DC current. Unlike AC current, in which the current is constantly moving between a maximum positive and maximum negative flows, DC current maintains a constant current flow. This allows for a PMF in which the magnetic field strength alternates between a constant maximum strength in a single polarity and zero when the magnetic field is off. The magnetic field is maintained at a predetermined maximum field strength for a predetermined amount of time, and is then maintained at zero for a predetermined amount of time. In other words, the magnetic field is maintain "on" for a first period of time and is then maintained "off" for a second period of time which can be the same or different from the first period of time.

Figure 2:
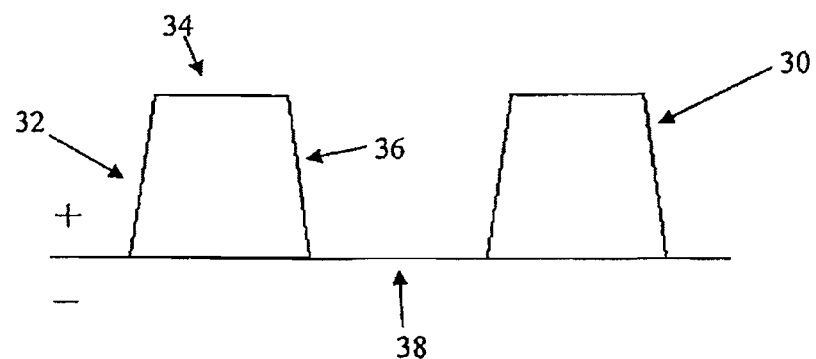
FIG. 2 is a schematic illustrated a wave form of a PMF according to one embodiment of the present invention.

FIG. 2 shows an exemplary magnetic field wave form 30 of a PMF generated by DC current according to the present invention. The wave form 30 includes four separate phases, namely, a) a rising phase 32, b) a steady maximum phase 34, c) a falling phase 36, and d) a steady zero phase 38. For example and according to one embodiment, a PMF according to the present invention can alternate between a maximum magnetic field strength of about 15 mT and about 0 mT at a frequency of about 0.16 Hz; however, the field strength and frequency can be other values as described below.

Methods for establishing a PMF are well known in the art, and according to the present invention, any number of conventional methods can be used to generate the desired PMF wave form so long as it based on DC current. One example of such a method utilizes a coiled wire. When a current is applied to the coil, a magnetic field is created around the coil. When the current is removed from the coil, the magnetic field ceases to exist. Therefore, by alternately applying a current to and removing a current from a coiled wire at a predetermined frequency, a PMF is created.

As described above, a PMF is typically generated as a result of AC current flowing through a magnetic field generating element, such as a coiled wire, to generate the wave form illustrated in FIG. 1a. Since the PMF according to the present invention is generated by DC current, if the power supply being used is an AC power supply, a converter can be utilized to convert the AC current to DC current before it flows through the magnetic field generating element (coiled wire).

As previously mentioned, the present invention is directed towards a method of improving neuronal performance by exposing a target nerve of a patient to a PMF generated by a DC current. The nerve can be associated with the central nervous system or associated with the peripheral nervous system. Preferably, the nerve is associated with the peripheral nervous system. It has been observed that when the target nerve is exposed to a PMF generated from a DC current having a predetermined frequency at a predetermined magnetic field strength, the transmission of the compound action potential through that target nerve is advantageously improved. This result in an increase of the amplitude of the action potential for a given stimulant when compared to the action potential for that stimulant in the nerve prior to the exposure to the PMF. As is known, if the amplitude of the compound action potential does not cross a threshold, the nerve does not function in a normal manner and the motor skills of the patient can be diminished or completely lost in a given area since, for example, muscle contraction in the given area may be lost.

The amplitude of the compound action potential gradually increases as the nerve is exposed to a PMF generated by DC current according to the present invention. Furthermore, the increase in the amplitude of the compound action potential is sustained over a period of time after exposure to the PMF and after removal of the PMF. The length of the period of time where improved neuronal performance is realized depends on a number of different parameters, such as characteristics of the PMF and the length of exposure of the target nerve to the PMF.

It will be appreciated that different PMFs generated by DC current improve the performance of neurons to different degrees depending on a number of different parameters including the type of target nerve, its location, etc. More particularly, optimization of the neuronal performance enhancement depends on the parameters of the PMF, such as the field strength and frequency. Additionally, the length of time in which the nerve is exposed to PMF will affect the enhancement of neuronal performance. The present inventors have discovered a set of parameters for the PMFs that are capable of enhancing neuronal performance. The enhancement can easily be measured by the increase of the amplitude of the compound action potential for a given stimulant when the nerve is exposed to a PMF when compared to the performance of nerve prior to the PMF exposure. The measurements of the amplitude of the compound action potential can be made after the nerve has been exposed to a PMF for a predetermined amount of time.

The PMF of the present invention has a predetermined frequency and a predetermined field strength so that the after a predetermined amount of time of exposure to the PMF, the amplitude of the compound action potential is increased a predetermined amount. The increase in amplitude of the compound action potential is preferably by at least 10% compared to the amplitude of the compound action potential before application of the PMF of the present invention. Preferably the amplitude of the compound action potential is increased by at least 25%. More preferably, the amplitude of the compound action potential is increased by at least 50%. Even more preferably, the amplitude of the compound action potential is increased by at least 100%. The field strength is typically measured at the location of the nerve.

The PMF of the present invention has a predetermined frequency so that exposure to the PMF causes the amplitude of the compound action potential to increase. The actual frequency that will achieve the best results varies with the particular target nerve and the magnetic field strength. In one embodiment of the invention, the frequency of the PMF is less than 0.5 Hz. In another embodiment, the frequency is between about 1 Hz and about 0.05 Hz or between 0.16 Hz and 0.5 Hz. In addition, the frequency can be about 1 Hz, about 0.5 Hz, or about 0.16 Hz. In an alternate embodiment of the invention, the frequency is at least about 0.5 Hz.

The PMF of the present invention have a predetermined magnetic field strength so that exposure to the PMF causes the amplitude of the compound action potential to increase. The actual magnetic field strength that will achieve the best results varies with the particular target nerve and the frequency of the PMF. In one embodiment of the invention, the magnetic field strength of the PMF is less than about 100 mT, less than about 50 mT, less than about 25 mT or less than about 15 mT. Preferably, a range of the magnetic field strength is between about 25 mT and 10 mT. Even more preferably, the magnetic field strength is from about 15 mT to about 12 mT. Even more preferably, the magnetic field strength is about 15 mT or about 12 mT.

Figure 3:
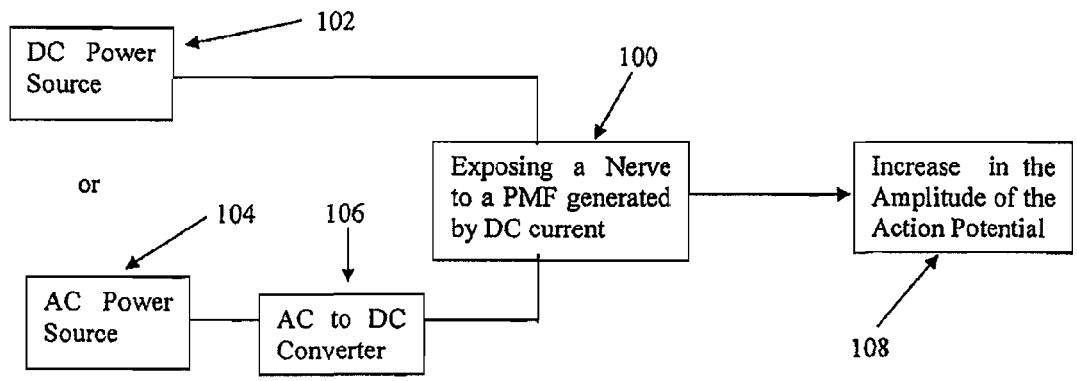
FIG. 3 is a schematic block diagram illustrating one exemplary method according to the present invention for improving neuronal performance.

FIG. 3 shows a block diagram 100 illustrating one exemplary method according to the present invention. Block 100 depicts the step of exposing a target nerve to a PMF generated by DC current according to the present invention. The DC current can be supplied by a DC power source 102 or alternatively, the DC current is supplied by an AC power source 104 which provides AC current that is converted to DC current in an AC/DC converter 106. The parameters (characteristics or properties) of the PMF, such as the associated frequency and magnetic field strength, are controlled so that the exposure to the PMF causes the target nerve to experience an increase in the amplitude of its compound action potential.

Another aspect of the present invention relates to the means or manner in which the PMF of the present invention is generated and applied to target nerve. More particularly and according to the present invention, any number of different apparatuses can be provided for applying the PMF, with the type of apparatus and its construction depending, in part, upon where the target nerve is located and also the location where the treatment will occur.

Figure 4:
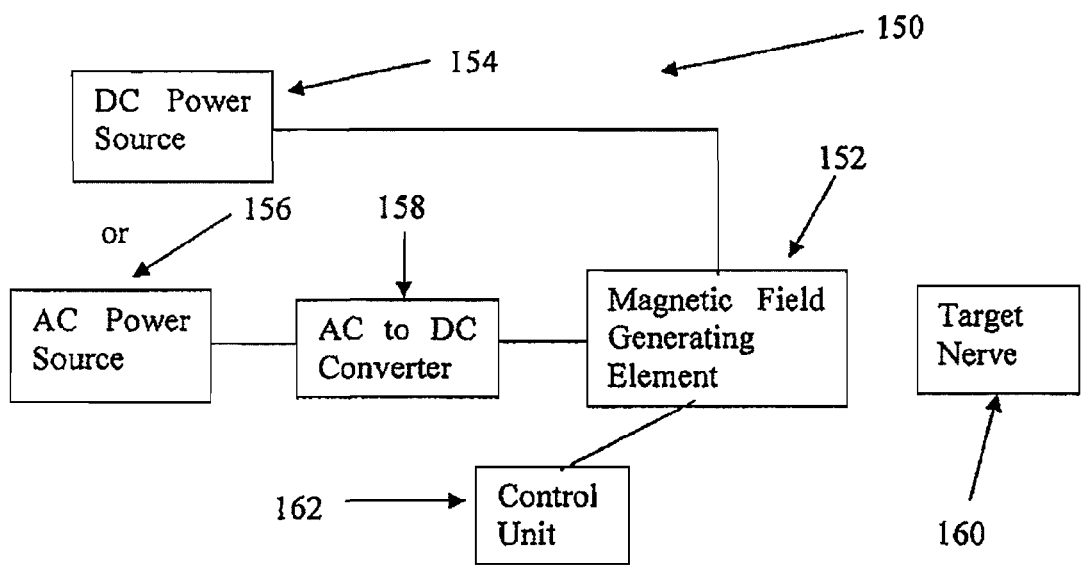
FIG. 4 is schematic block diagram illustrating one exemplary apparatus according to the present invention for improving neuronal performance.

FIG. 4 is a schematic diagram of one exemplary apparatus 150 according to the present invention for applying the PMF to a target nerve 160. The apparatus 150 contains a magnetic field generating element 152 which receives an electrical current, in this case DC current. Magnetic field generating elements 152 are well known in the art, and according to the present invention, any number of elements can be used. One example of a suitable magnetic field generating element 152 is a magnetic coil through which an electrical current (DC current) can flow. Magnetic coils are typically circular, however, other coiled shapes and configurations are equally possible. Another example of a magnetic field generating element 152 is a straight electrical wire, through which an electrical current (DC current) can flow.

The magnetic field strength of the apparatus 150 varies as the amount of current flowing through the magnetic field generating element 152 varies and as the distance from the target nerve 160 to the element 152 varies. In general, a greater electrical current will generate a stronger magnetic field. Additionally, the magnetic field will be stronger at locations closer to the element 152. However, there are exceptions to this rule, such as inside a coil magnet. According to the present invention, the electric field strength can be adjusted to a predetermined strength which is effective in enhancing neuronal performance by adjusting the electrical current and by varying the distance of the nerve 160 from the element 152.

The electrical current flowing through the magnetic field generating element 152 must be DC current according to the present invention in order to achieve the beneficial and advantageous results described herein. However, the current can be supplied by a DC power source 154 or an AC power source 156. When the AC power source 156 is used, a converter 158 is utilized to convert the AC current to DC current before the current flows through the magnetic field generating element 152.

Furthermore, the power source can be portable or non-portable. Different power sources are well known in the art, and according to the present invention, a number of power sources can be used. An example of a portable power source is a battery, which typically supplies a DC current and therefore can be directly attached to the magnetic field generating element 152 to supply DC current thereto. An example of a non-portable power source is an electrical outlet. In the U.S., electrical outlets provide AC current and therefore, when using an electrical outlet in the U.S., converter 158 is utilized to convert the AC current to DC current. The apparatus 150 can also include a control unit 162 (controller), through which the current through the magnetic field generating element and the PMF frequency can be controlled.

Preferably, the control unit 162 is of a programmable type in one embodiment to permit the operator to enter information relevant for the treatment of the nerve and/or selection of the operating parameters of the apparatus 150. For example, the operator, who may be a physician or the patient themselves, can input the desired magnetic field strength and the frequency. In addition, a time period for the length of the treatment can be inputted into the controller and based on this inputted information, the controller 162 can operate the magnetic field element 152 in a manner that results in the desired PMF being generated.

Preferably, the control unit 162 is in the form of a digital interface to permit easy entry of information.

Figure 5A:
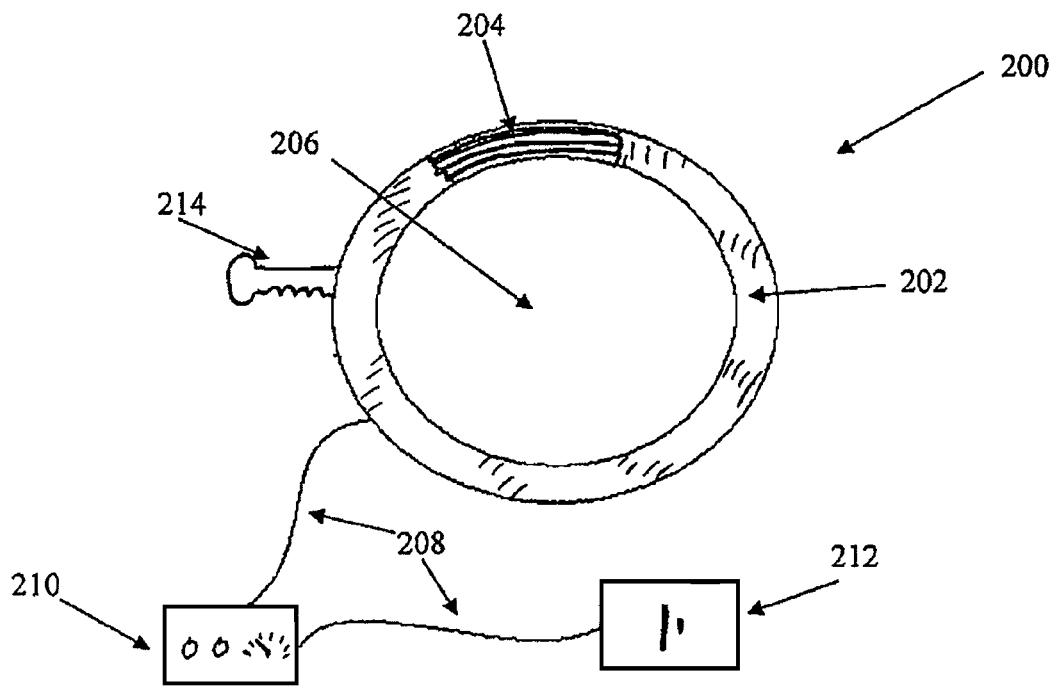
FIG. 5a is an end view of a ring-shaped apparatus according to one exemplary embodiment of the present invention and for insertion of a target body therein.
Figure 5B:
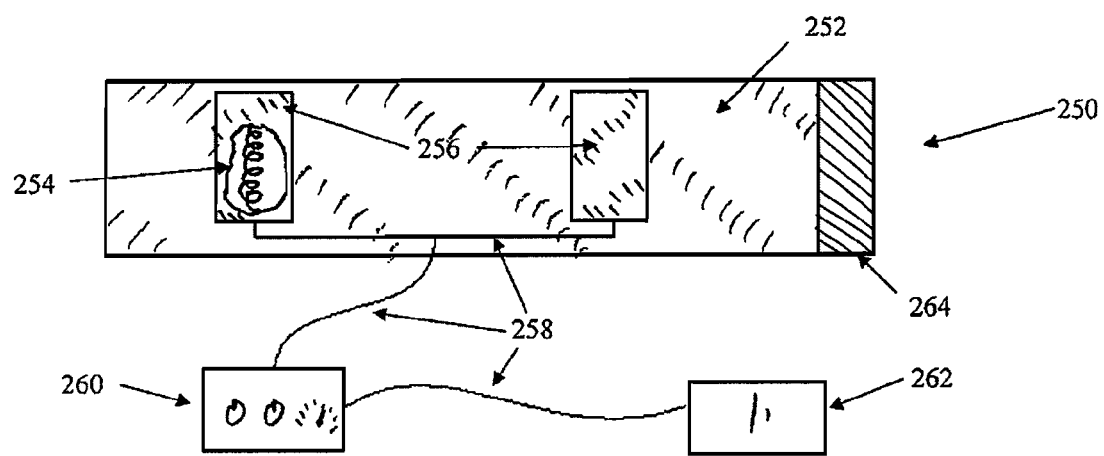
FIG. 5b is a side elevation view of a flexible band according to one exemplary embodiment and for placement against a target body.

In addition, the user interface can include interactive, illustrative icon buttons that depict general locations of the target nerve 160 and also a set of interactive illustrative icon buttons can be presented that depict the type of apparatus being used with the controller 162 since it will be appreciated and understood that the controller 162 can be used with a number of different apparatuses, such as those illustrated in FIGS. 5a and 5b. Accordingly, the user interface can include icons that depict various parts of the human body, such as an arm or leg or a torso to which the apparatus 150 is to be applied and which generally represents the location of the target nerve. Similarly, the user interface can include icons that illustrate the different types of apparatuses for applying the PMF, e.g., a ring-shaped band, an open ended, flexible band or two separate pads for placement on the body with the target nerve 160 lying therebetween. The selection of the type of device can be programmed to provide any slight modification to the operating conditions so that optimization of the operating conditions is achieved.

In one embodiment, the controller will take the inputted target nerve location information and use it in calculating the necessary operating parameters of the PMF that will result in the inputted magnetic field strength at the target nerve itself. For example, the controller 162 can take into account if the target nerve 160 is deeper in the body of the patient and therefore, the distance from the target nerve to the magnetic field generating element 152 will be greater and this can influence the operating parameters of the PMF. In addition, the controller can be configured so that based on the inputted targeted body part that is selected with the user interface as by selecting one of the icons (that illustrates various body parts) of the user interface display, the controller will select the magnetic field strength, operating frequency and the time period for the treatment. In this manner, the user simply selects the body location that is to be treated and the controller then initiates the proper treatment for the patient based on stored operating parameters.

A treatment is defined as a length of time in which a nerve is exposed to a PMF. The present invention allows for various different treatment arrangements using PMFs of different strengths and frequencies. For example, according to one embodiment of the invention, each treatment is performed using a PMF generated by DC current having the same predetermined magnetic field strength and frequency. According to another embodiment of the invention, an initial treatment is performed using a PMF having a first predetermined field strength and frequency, and the several subsequent treatments are performed using a PMF having a second predetermined field strength and frequency. Therefore, one can perform an initial treatment using a stronger PMF and the following treatments could use a weaker PMF. It will also be understood that the control unit 162 can be configured to provide a multi-mode application in which the operator can select from one of the saved programs in which a first treatment mode using a PMF having a first predetermined field strength and frequency is first performed and then a second treatment mode using a PMF having a second predetermined field strength and frequency is subsequently performed. The time periods for each of these treatments is variable and can be selected by the operator. For example, the first treatment mode can be programmed to last more than 75% of the total time, with the second treatment mode simply being an ending treatment.

However, the control unit 162 can also be programmed so that the two treatments are separated by a significant amount of time and a timer of the control unit 162 can keep track of the time and then instructed the control unit 162 to send an alert, e.g., a chime or alarm, to the patient reminding the patient that the second treatment should be initiated. For example, one treatment program can call for a second treatment to be applied about 6-8 hours after the initial treatment and this second treatment can be at a different field strength and frequency than the first treatment. This second treatment can be thought of as a refresher treatment or the like and can last for a shorter time period than the first treatment.

It will also be appreciated that the above versatility and options allows for the use of a non-portable apparatus capable of creating a stronger PMF for the initial treatment, and the use of a portable apparatus for the subsequent treatments, providing the patient with great flexibility when designing a treatment schedule.

According to the present invention, the target nerve 160 is exposed to a PMF generated by DC current by placing the apparatus 150 in the vicinity of the target nerve 160 to be treated. The exact placement of the apparatus 150 will depend on the location of the nerve 160 to be treated, the overall shape of the apparatus and the particular magnetic field generating element used in the apparatus. For example, if the nerve 150 to be treated is in the arm of the patient, the arm can be placed through a circular apparatus with a large circular magnetic coil, which is described below with reference to FIG. 5a. The current through the coil can then be adjusted to produce a magnetic field with a predetermined magnetic field strength at the location of the nerve. Thus, the magnetic field strength that is entered into the programmable control unit 162 is the strength of the magnetic field that is to be found at or near the target nerve as opposed to the strength of the magnetic field at another location, such as the skin surface. Thus, when the control unit 162 has modes that can be selected to input the location of the target nerve 160, the control unit 162 can then take this inputted information into consideration when selecting the appropriate operating conditions that will result in the strength of the magnetic field being the predetermined, desired value at or near the target nerve 160 itself which is separated by a distance from the coiled wire. Thus, the control unit 162 takes into account this normal, typical distance of separation from the target nerve 160 and the coiled wire.

In an alternate embodiment, separate magnetic field generating elements 152, such as small magnetic coils, could be placed on opposite sides of the patient's arm, producing a PMF at the location of the nerve that is a combination of PMFs produced by each element. The elements could be part of the same apparatus, i.e., they may share the same power source and controls, or they may be separate apparatuses, each having their own power source and controls as described in more detail below.

In another example, if the nerve 150 to be treated is in an internal organ, such as the liver, a circular apparatus with a circular magnetic coil can be placed around the patients body (torso) so that it is located in substantially the same plane as the liver. Alternatively, separate magnetic field generating elements, such as small magnetic coils, could be placed around the patients abdomen, in substantially the same plane as the liver.

As previously mentioned, the method and apparatus of the present invention are useful in a treatment to enhance neuronal performance. This treatment is useful for people suffering from a disease or condition in which the transmission of the compound action potential is impaired. Examples of such diseases and conditions are neuropathies, such as, distal axonopathies, myelinopathies, neuronopathies and autonomic neuropathies and hyporeflexia and areflexia. This treatment is even useful in the regeneration of muscles or organs that have been considered paralyzed due to severe impairment of the compound action potential transmission. This treatment is also useful in enhancing the neuronal performance of an animal not suffering from any such disease or condition. Such a person could enhance the performance of a particular organ or muscle by enhancing the neuronal performance of that organ or limb. This treatment is also useful in relieving pain or to simply provide a person with a healthier feeling in a particular muscle or organ.

FIG. 5a depicts one embodiment of the apparatus of the present invention. The apparatus 200 includes a main body 202 which contains magnetic field generating element 204. The magnetic field generating element is a coiled wired. Preferably, the main body 202 is made of an insulating material, allowing the patient to touch the apparatus without risk of electric shock. A patient could place his or her limb (or even the torso) through the opening 206 of the main body 202 to perform a treatment on a target nerve located in that limb (or in the torso). Wires 208 connect the magnetic field generating element 204 to a control unit 210 and a power supply 212. The control unit 210 may include controls which allow the patient to adjust the current flowing through the magnetic field generating element and the frequency of the PMF (the control unit 210 can be similar or identical to control unit 162 and therefore include the above described features). If the power supply provides AC current, a converter can be used to convert the AC current to DC current. For simplicity, a converter is not shown in FIG. 5a. The apparatus may include a handle 214, by which the patient can hold the apparatus during treatments.

Alternatively and instead of a handle 214, the apparatus 200 can include a mounting element, such as a post or bracket, that can be releasably attached and coupled to a stand or the like in such a way that the apparatus 200 is supported by the stand but also, can be moved over a range of motion. For example, the attachment between the apparatus and the stand can be of a pivotal nature such that the apparatus 200 can be pivoted relative to the stand and preferably can be rotated also relative to the stand to permit, the operator or patient to move the apparatus 200 over a range of motion to permit the apparatus 200 to be moved to a proper location where the target nerve lies therebetween. For example, the patient can lie on a bed or treatment table and then the apparatus 200 can be manipulated so as to position the limb or torso of the patient within the body 202.

It will be appreciated that the apparatus 200 can be constructed to be of a portable type in that the control unit 210 and the power supply 212 can be incorporated into a portable pack or the like to which the body 202 is connected via electrical wire 208. In this case, the power supply 212 will be a DC battery that can be housed in a compartment that is part of a control module that includes the control unit 212 and some type of display to display information, such as the values of the magnetic filed, the frequency, etc., and preferably, the control module will have a user interface, such as a keypad that permits entry of the information.

FIG. 5b depicts a second embodiment of an apparatus 250 of the invention. The apparatus 250 includes magnetic field units 256 which are attached to main body 252. The magnetic field units 256 each contains a magnetic field generating element 254 (only one is illustrated in FIG. 5(b)). The magnetic field generating elements 254 are preferably coiled wires. Preferably, the magnetic field units 256 and the main body 252 are made of an insulating material, allowing the patient to touch the apparatus 250 without risk of electric shock.

The body 252 can be in the form of a flexible body that can readily bend in areas, especially the areas surrounding the units 256 and in the illustrated embodiment, the body 252 is in the form of an elongated flexible band that can be made of synthetic material, etc., that can readily be bent so as to shape the body 252 to the shape of the patient's body and in particular, to the target area of the patient, such as a limb or torso. A patient can thus wrap the main body 252 around a limb on his or her body or around his or her torso, to perform a treatment on a nerve in that limb or torso.

This would allow for each magnetic field generating unit 254 to be placed in separate locations in the vicinity of the nerve. One or more wires 258 connect both magnetic field generating elements 254 to a control unit 260 and a power supply 262.

The control unit 260 can include controls which allow the patient to adjust the current flowing through the magnetic field generating element and the frequency of the PMF and can function and have the features previously described with reference to control unit 162. If the power supply 262 provides AC current, a converter can be used to convert the AC current to DC current. For simplicity, a converter is not shown in FIG. 5b.

The apparatus 250 preferably includes some type of means for holding and maintaining the body 252 on the patient. For example, the body 252 can include a strip of hook and loop type material 264, which the patient can adhere to a part of the main body 252, holding the apparatus 250 in place during treatments.

In yet another aspect of the present invention and according to another embodiment of the present invention, each of the units 256 includes a releasable fastening means, such as a hook and loop fastener, that mates with a complementary fastener that is part of the body 252 to permit the units 256 to be securely fastened to the body 252 yet readily repositioned thereon to permit difference not only different orientations of the units 256 but also different positions between the units 256. Thus, in the case of a hook and loop type fastening system, one of the fastening elements (e.g., pads or strips of hook and loop type material) is associated and coupled to the unit 256 and the other of the fastening elements (e.g., pads or strips of hook and loop type material) is associated and coupled to one face/surface of the body 252. For example, the entire front surface of the body 252 that faces the patient in use can have a layer of hook and loop type material and this permits the units 256 with their hook and loop type material facing this layer to be able to be readily attached and repositioned along the front surface. This permits strategic placement of the units 256 so as to better position the target nerve between the two units 256. For example, a larger sized patient may require a greater distance of spacing between the two units 256 then a smaller patient. This embodiments permits such customization.

EXAMPLE 1

A segment of a mouse somatic nerve (sciatic nerve) was isolated. The nerve was placed in a chamber surrounded by a coiled wire. The coiled wire was connected to an electrical outlet supplying AC current, which was converted by a converter to DC current. The flow of current through the coil was regulated by a computerized timer.

In order to mimic in vivo conditions, the nerve was electrically stimulated every 30 seconds to evoke a compound action potential. The electrical stimulations continued throughout the experiment, i.e., before the PMF was activated, while the PMF was activated and after the PMF was deactivated. The amplitude of the compound action potential was measured and recorded by the computer throughout the experiment. After a short period of time, the response of the nerve stabilized, i.e., the compound action potential of the nerve remained about the same for each subsequent electrical stimulation. At this point the PMF was activated for about 30 minutes. The magnetic field strength at the location of the nerve was about 15 mT and the frequency of the PMF was set to 0.16 Hz. The PMF was then deactivated, and for the remainder of the experiment, the nerve was electrically stimulated and the compound action potential was recorded without the PMF.

Figure 6A:
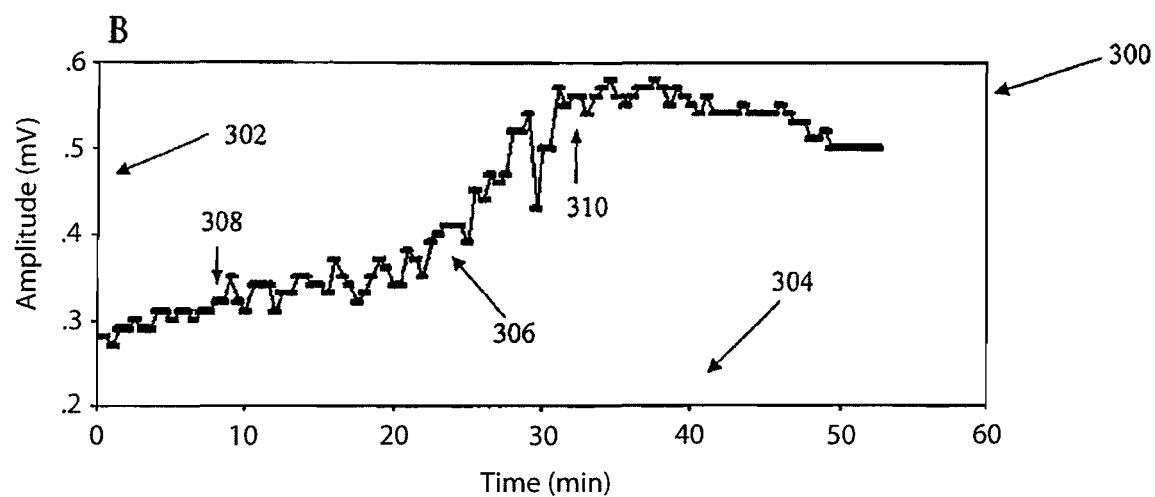
FIG. 6a is a depicts a graph showing the amplitude of the compound action potential vs. time of the nerve of Example 1.

FIG. 6a shows a graph 300 depicting the results of this experiment. Y-axis 302 depicts the amplitude of the compound action potential in milivolts and x-axis 304 depicts time in minutes. Line 306 shows the compound action potential of the nerve as it was measured throughout the experiment. At point 308 the PMF was activated. At point 310 the PMF was deactivated. It is evident from the segment of line 306 between points 308 and 310 that the exposure to the PMF increased the compound action potential of the nerve. It is evident from the segment of line 306 after point 310 that the increased compound action potential was sustained even after the PMF was deactivated.

Figure 6B:
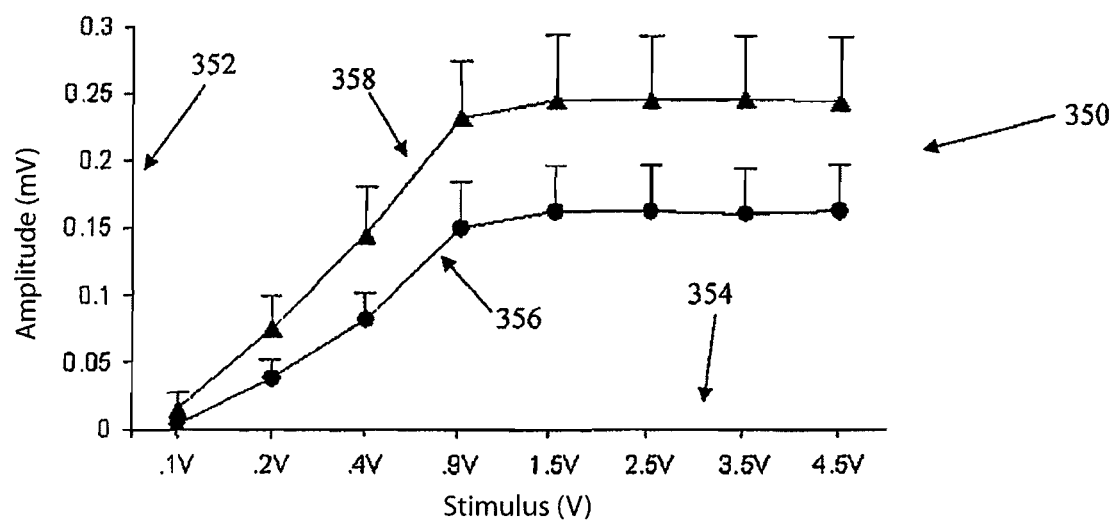
FIG. 6b is a graph showing the amplitude of the compound action potential vs. the potential of the electrical stimulus for the nerve of Example 1 before and after exposure to the steady PMF.

FIG. 6b shows a graph 350 depicting the amplitude of the compound action potential of the nerve for different stimuli before and after the nerve is exposed to the PMF. Y-axis 352 depicts the amplitude of the compound action potential in milivolts and x-axis 354 depicts the voltage of the stimulus in volts. Line 354 shows the amplitude of the compound action potential for different stimuli before exposure to the PMF. Line 354 shows the amplitude of the compound action potential after the exposure to the PMF. It is evident that threshold of the electrical stimulus, i.e., the minimum strength of the stimulus to induce a compound action potential with a particular amplitude, was significantly reduced.

EXAMPLE 2

Figure 7A:
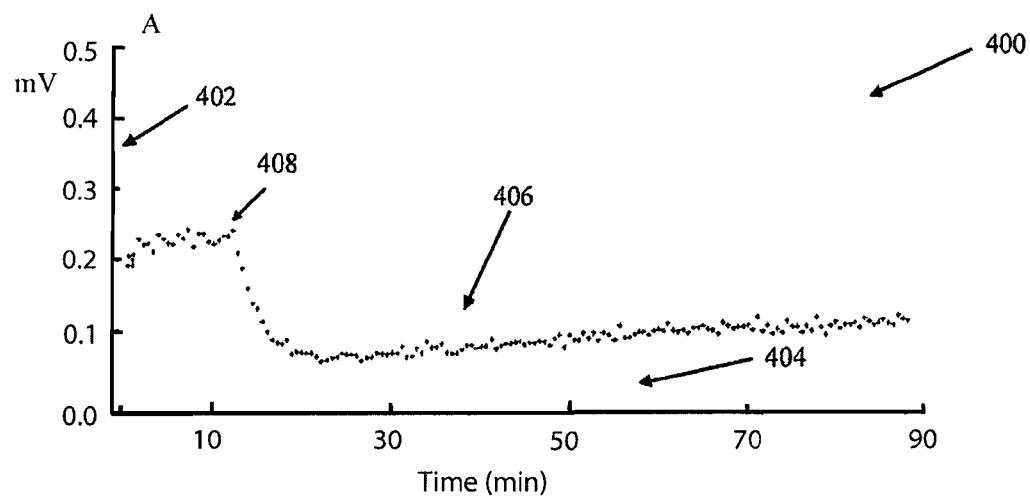
FIG. 7a is a graph showing the amplitude of the compound action potential vs. time for the control nerve of Example 2.

A further experiment was performed using the same method and apparatus of Example 1. In this experiment, lidocaine was administered to the nerve after the nerve's response to the electrical stimulation stabilized. Lidocaine has a suppressive effect on the compound action potential, and the amplitude of the compound action potential of the nerve decreased significantly. FIG. 7a shows a graph 400 which depicts the results of a control study, showing the effect of lidocaine on the compound action potential. Y-axis 402 depicts the amplitude of the compound action potential in milivolts and x-axis 404 depicts time in minutes. Line 406 depicts the compound action potential of the nerve. 150 uM of lidocaine is administered to the nerve at point 408. The segment of line 406 before point 408 depicts the compound action potential of the nerve prior to the administration of lidocaine. The segment of line 406 after point 408 depicts the compound action potential of the nerve after the administration of lidocaine. It is evident that the amplitude of the compound action potential decreases significantly as a result of the administration of lidocaine. This mimics a nerve suffering from a disease or condition that impairs the transmission of the compound action potential. The PMF was then activated, and the experiment was performed as described in Example 1. Due to the exposure to the PMF, the amplitude of the compound action potential increased to amplitudes greater than the pre-lidocaine, pre-PMF exposure level.

Figure 7B:
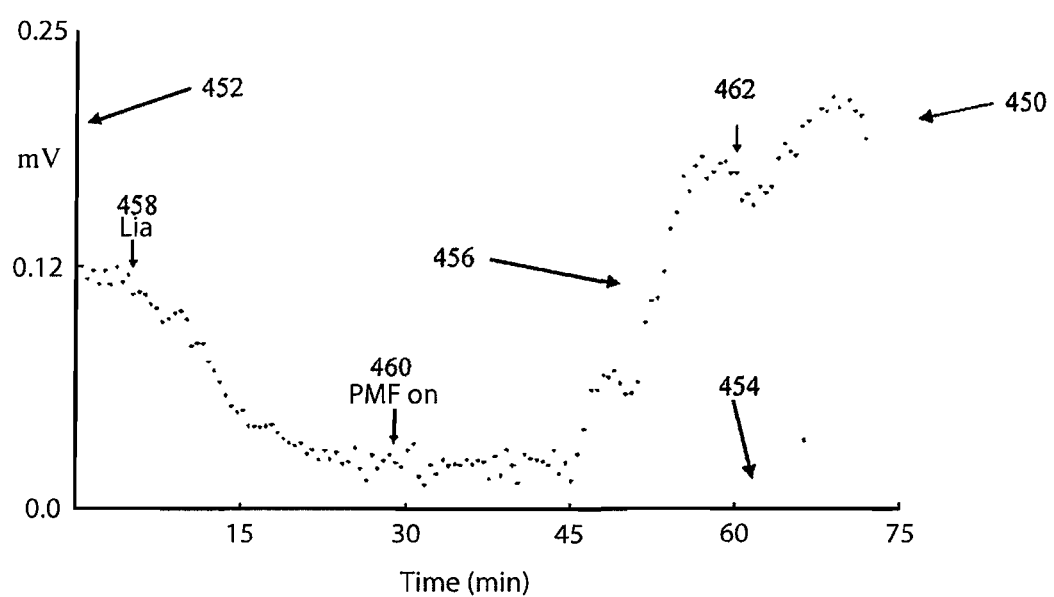
FIG. 7b is a graph showing the amplitude of the compound action potential vs. time of the nerve of Example 2.

FIG. 7b shows graph 450 depicting the results of this experiment. Y-axis 452 depicts the amplitude of the compound action potential in milivolts and x-axis 454 depicts time in minutes. Line 456 shows the amplitude of the compound action potential throughout the experiment. At point 458, lidocaine was administered to the nerve. At point 460 the PMF was activated, and at point 462, the PMF was deactivated. It is evident from the segment of line 456 between point 458 and 460 that the lidocaine decreased the compound action potential. It is evident from the segment of line 456 between points 460 and 462 that exposure to the PMF increased the compound action potential to amplitudes even greater that before the lidocaine was administered. And it is evident from the segment of line 456 after point 462 that the increase in the amplitude of the compound action potential was sustained after the PMF was deactivated. This demonstrates that through exposure to a PMF generated by DC current, it is possible to enhance the performance of a nerve suffering from a disease or condition that impairs the transmission of the compound action potential.

EXAMPLE 3

Figure 8:
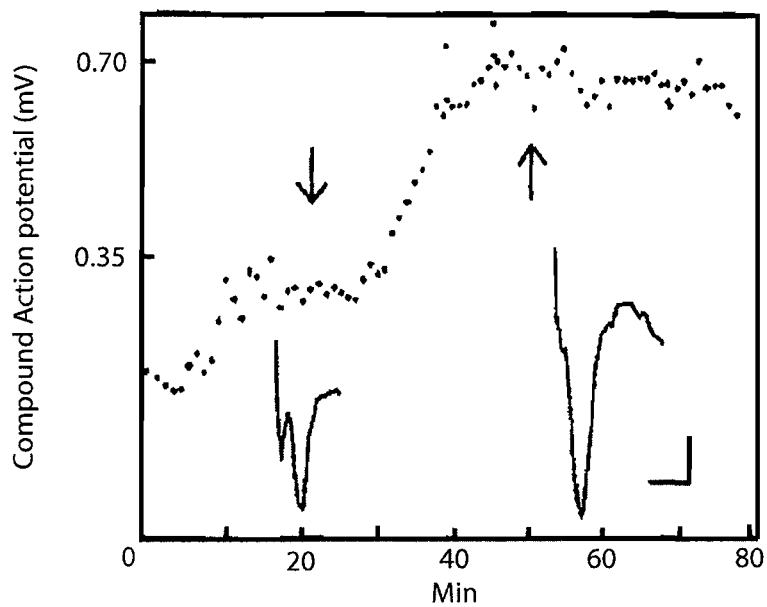
FIG. 8 is a graph showing the amplitude of the compound action potential vs. time for the spinal cord segment of Example 3.

The influence of the PMF, according to the present invention, on the compound action potential recorded from a spinal cord sample is illustrated in the graph of FIG. 8. In particular, segments of the spinal cord were prepared as described in the Agrawal and Fehlings reference incorporated above. Following decapitation and laminectomy, a thoracic segment of the spinal cord (20-30 mm) was removed and placed in cold Ringer's solution. Subsequently, the dorsal column was cut longitudinally (to form a hemisection) and this sample was placed in the recording chamber. The stimulating and recording electrodes were located on both ends of the preparation. Following a preincubation period, the cut samples were individually transferred to the recording chamber and the compound action potential (CAP) was followed for several minutes to achieve a stable recording. Then, the preparation was exposed to a PMF for a time period of 30 minutes at a frequency of about 0.16 Hz.

FIG. 8 depicts the results of this testing procedure and in particular, the graph shows the influence of the PMF on the compound action potential recorded from a spinal cord sample. "PMF On" and "PMF Off" indicate the beginning and end of the exposure of the 0.16 Hz PMF. As shown, the amplitude of the compound action potential from the spinal cord was elevated by 232%±19%.

EXAMPLE 4

Figure 9:
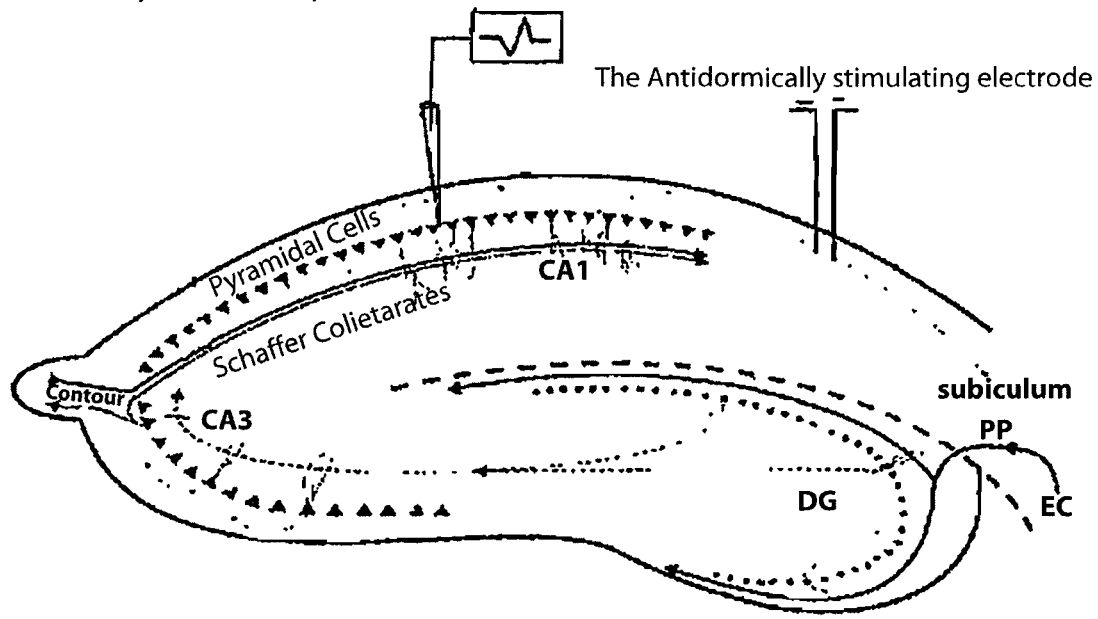
FIG. 9 is a diagram showing an experimental arrangement to record compound antidromic potentials from hippocampal slices.
Figure 10:
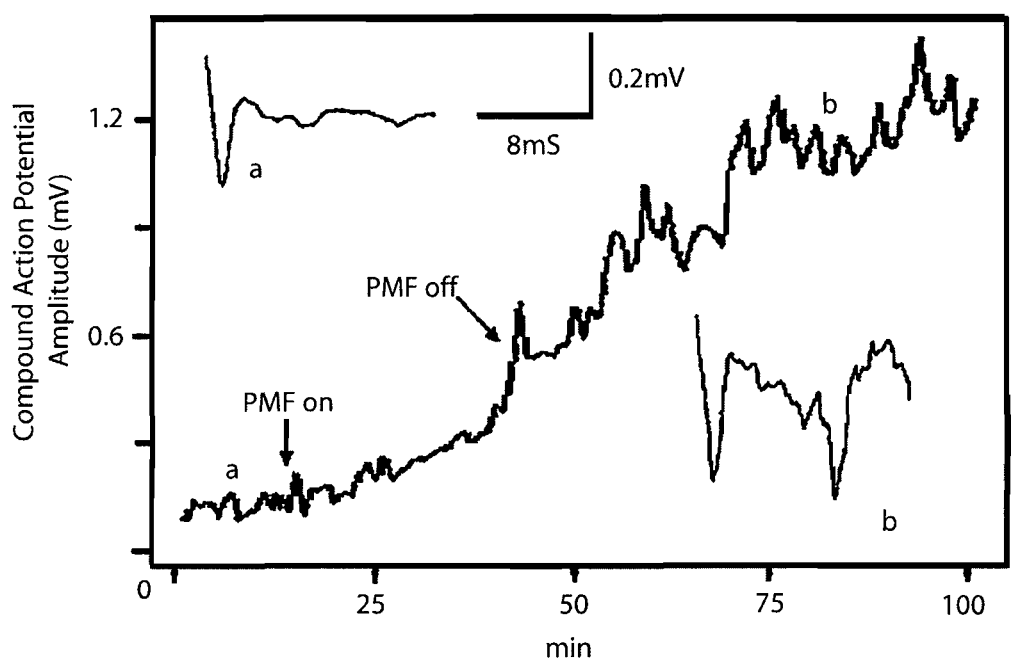
FIG. 10 is a graph showing the effect of PMF on the antidromically-evoked potential recorded from a specimen of Example 4.

FIG. 9 shows the effect of PMF on antidromically evoked compound action potential (CAP) recorded from hippocampal slices taken from a brain. The hippocampal slices were prepared according to the standard procedure disclosed in the Wieraszko reference previously incorporated. The arrangement of the antidromically stimulating electrode and the electrode recording antidromic compound action potential (CAP) is depicted in the graph of FIG. 9. The influence of PMF on antidromically evoked potentials is shown in FIG. 10. The hippocampal slices were incubated in a calcium free medium and with 2 mM kynurenic acid. Addition of kynurenic acid (blocker of glutamergic receptors) to the slice containing chamber and the omission of calcium eliminate any contribution of glutamergic synaptic transmission to the generation of the recorded potentials. The graph of FIG. 10 shows the amplitude of the population spikes during the entire trial run. The results show that the PMF has increased significantly the size of the population spike and in particular, the amplitude of the CAP increased significantly, e.g., 183%±11%.

The present invention has widespread applicability since the present invention provides an apparatus and method of pulsed magnetic field to treat pathologies of the peripheral nerve system. Since the present invention dramatically improves the propagation of the compound action potential along the axon, the present invention can be applied in pathological conditions, expressed as an impairment of this propagation. Therefore, the PMF methods of the present invention can be used to treat the following pathological conditions:

1. Neuropathies: conditions generally classified as symmetric generalized neuropathies (polyneuropathies), which are further classified into: distal axonopathies (in case of diabetes), myelinopathies, neuronopathies (amyotrophic laterial sclerosis, known as ALS and hereditary dysautonomia). All of these neuropathies are characterized by significant reduction in the ability of the nerves to generate and to conduct a compound action potential.

2. Joint pathologies: denervation of joints in some diseases (Charcot's neuropathy) leads to severe osteoarthritic changes in the affected joints. This indicated that proper innervation of the joint is vital for its function. Even a subtle reduction in nerve conductions or changes in innervations can cause osteoartheritic changes in the affected joints. Increasing the excitability of the nerves around the joint can exert a trophic effect improving its viability. It may also enhance the regeneration of the cartilage simulating cartilage-producing cells (chondrocytes). PMF simulation can also restore the joints viability by increasing the activity of the nerves innervating this particular joint.

3. Nerve regeneration. It is known that sustained neuronal activity is essential for nerve regeneration and for re-establishing damaged innervation of the internal organs. Therefore, PMF-induced increase in neuronal excitability of the peripheral nerves, or spinal cord following injury to each or both could increase the nerve capability to regenerate and restore lost contact with target organs, and to improve propagation of compound action potentials within the spinal cord.

4. Hypo- and areflexia. These are pathologies that are expressed as weak or absent reflexes. Very often these pathologies are related to deficits in transmission of information in the spinal cord, or diminished efficiency of the peripheral nerves to transmit a compound action potential, and PMF exposure could restore the strength of the reflex.

5. A chronic Bell's palsy: This pathology, expressed as facial nerve paralysis is currently incurable. Increasing the excitability of the facial tissue by exposure to PMF could have a great potential to cure such condition.

6. Selective stimulation of internal organs: Magnetic stimulation of the autonomic nerves or ganglion can specifically enhance the function of an organ innervated by stimulated nerve or ganglion. For example, exposure of the colon to PMF could increase its enteric system excitability to treat a patient with irritable bowel. Increasing the excitability of the sacral region could improve the function of several organs of the pelvic region. In a patient with weak cardiac output, which is usually due to low compound action potential, exposure to PMF could offer a treatment solution.

7. Channelopathies. The mechanism of generation and propagation of the action potential is linked to the function of specific structures in the membrane of the nerve cells called ion channels. These channels allow ions, like sodium, potassium, calcium and chloride to diffuse in and out of the cell. Several disorders of the nervous system are related to pathology of these channels. These pathologies are collectively called "channelopathies". Applicant has discovered that the action of PMF in mostly exerted through modulation of the function of the sodium channels.

Although some embodiments of the invention has been shown and described, many features may be varied, as will readily be apparent to those skilled in this art. Thus, the foregoing description is illustrative and not limiting, the invention being defined by the following claims.

What is claimed:

1. A method for improving neuronal performance of a target nerve of a patient, comprising:
   exposing the target nerve to a pulsed magnetic field generated by DC current having a predetermined magnetic field strength at a predetermined frequency; the pulsed magnetic field, in one cycle time, being the predetermined magnetic field strength for a first predetermined time and substantially zero for a second predetermined time; and
   increasing an amplitude of a compound action potential of the target nerve and maintaining an increase for a first time period after the pulsed magnetic field is stopped, the first time period being greater than a time period that the nerve is exposed to the pulsed magnetic field, increasing and maintaining being accomplished by controlling the magnetic field such that a strength of the magnetic field surrounding the target nerve is between about 15 mT and 25 mT at a frequency of between about 0.16 Hz and 0.5 Hz; the compound action potential being an electrical signal traveling through the target nerve; wherein the amplitude of the compound action potential is increased by at least about 25%.

2. The method of claim 1, wherein exposing the nerve comprises:
   supplying the DC current from a portable DC power source comprising a battery.

3. The method of claim 1, wherein exposing the nerve comprises:
   supplying AC current from an AC power source; and
   converting the AC current to the DC current using an AC/DC converter.

4. The method of claim 1, wherein the time period is greater than 1 hour.

5. The method of claim 1, wherein the time period is greater than 6 hours.

6. A method for improving neuronal performance of a target nerve of a patient, comprising:
   exposing the target nerve to a pulsed magnetic field generated by DC current having a predetermined magnetic field strength at a predetermined frequency; the pulsed magnetic field, in one cycle time, being the predetermined magnetic field strength for a first predetermined time and substantially zero for a second predetermined time; and
   increasing an amplitude of a compound action potential of the target nerve and maintaining an increasing for a first time period after the poled magnetic field is stopped, the first time period being greater than a time period that the nerve is exposed to the pulsed magnetic field, increasing and maintaining being accomplished by controlling the magnetic field such that a strength of the magnetic field surrounding the target nerve is between about 15 mT and 25 mT at a frequency of between about 0.16 Hz and 0.5 Hz; the compound action potential being an electrical signal traveling through the target nerve; wherein the amplitude of the compound action potential is increased by at least about 50%.

7. The method of claim 6, wherein exposing the nerve comprises:
   supplying the DC current from a portable DC power source comprising a battery.

8. The method of claim 6, wherein exposing the nerve comprises:
   supplying AC current from an AC power source; and
   converting the AC current to the DC current using an AC/DC converter.

9. The method of claim 6, wherein the time period is greater than 1 hour.

10. The method of claim 6, wherein the time period is greater than 6 hours.

11. A method for improving neuronal performance of a target nerve of a patient, comprising:
    exposing the target nerve to a pulsed magnetic field generated by DC current having a predetermined magnetic field strength at a predetermined frequency; the pulsed magnetic field, in one cycle time, being the predetermined magnetic field strength for a first predetermined time and substantially zero for a second predetermined time; and
    increasing an amplitude of a compound action potential of the target nerve and maintaining an increasing for a first time period after the pulsed magnetic field is stopped, the first time period being greater than a time period that the nerve is exposed to the pulsed magnetic field, increasing and maintaining being accomplished by controlling the magnetic field such that a strength of the magnetic field surrounding the target nerve is between about 15 mT and 25 mT at a frequency of between about 0.16 Hz and 0.5 Hz; the compound action potential being an electrical signal traveling through the target nerve; wherein the amplitude of the compound action potential is increased by at least about 100%.

12. The method of claim 11, wherein exposing the nerve comprises:
    supplying the DC current from a portable DC power source comprising a battery.

13. The method of claim 11, wherein exposing the nerve comprises:
    supplying AC current from an AC power source; and
    converting the AC current to the DC current using an AC/DC converter.

14. The method of claim 11, wherein the time period is greater than 1 hour.

15. The method of claim 11, wherein the time period is greater than 6 hours.

16. A method for treating a medical condition in which the neuronal performance of a patient is impaired, comprising:
    improving the propagation of a compound action potential along an axon of the patient's nervous system by exposing a target nerve to a pulsed magnetic field generated by DC current;
    the pulsed magnetic field, in one cycle time, being the predetermined magnetic field strength for a first predetermined time and substantially zero for a second predetermined time; and
    increasing an amplitude of the compound action potential of the target nerve and maintaining an increase for a first time period after the pulsed magnetic field is stopped, the first time period being greater than a time period that the nerve is exposed to the pulsed magnetic field, increasing and maintaining being accomplished by controlling the magnetic field such that a strength of the magnetic field surrounding the target nerve is between greater than 15 mT to about 25 mT at a frequency of between about 0.16 Hz to less than 0.5 Hz; the compound action potential being an electrical signal traveling through the target nerve.

17. The method of claim 16, wherein the medical condition is a pathological condition associated with one of the peripheral nervous system of the patient and the central nervous system of the patient.

18. The method of claim 16, wherein the medical condition is a pathological condition selected from the group consisting essentially of: neuropathies, joint pathologies, hypo- and areflexia, a chronic Bell's palsy, and charmelopathies.

19. The method of claim 16, wherein improving the propagation of a compound action potential along an axon of the patient's nervous system is part of one of a nerve regeneration treatment and a treatment for selective stimulation of an internal organ.

20. The method of claim 16, wherein the axon is part of the spinal cord of the patient.

21. An apparatus for improving neuronal performance of a target nerve of a patient, comprising:
a body for placement proximate to the target nerve, the body having at least one magnetic field generation element that receives DC current and generates a pulsed magnetic field having a predetermined magnetic field strength at a predetermined frequency, the pulsed magnetic field, in one cycle time, being the predetermined magnetic field strength for a first predetermined time and substantially zero for a second predetermined time;
the predetermined magnetic field strength and the predetermined frequency being selected such that an amplitude of a compound action potential of the target nerve increases as a result of exposure to the pulsed magnetic field and remains elevated for a time period after the exposure has ended; the compound action potential being an electrical signal traveling through the target nerve; and
a programmable control unit for controlling the predetermined magnetic field strength and the predetermined frequency, the programmable control unit including a user interface that includes one or more selectors for selecting a first mode that operates at one magnetic field strength and frequency and another mode that operates at another magnetic field strength and frequency.

22. The apparatus of claim 21, wherein the at least one magnetic field generating element is a coiled wire.

23. The apparatus of claim 22, wherein the coiled wire is constructed so that it can completely surround the target nerve in one plane.

24. The apparatus of claim 22, wherein the at least one magnetic field generating element comprises a pair of magnetic field generating elements spaced apart from one another to permit the target nerve to be positioned between the pair of magnetic field generating elements.

25. The apparatus of claim 22, further comprising a battery pack that serves as a power source for providing the DC current.

26. The apparatus of claim 22, further comprising a converter for converting AC current into the DC current that is received by the at least one magnetic field generating element.

27. The apparatus of claim 21, wherein the user interface is configured to permit a user to enter a location of the target nerve and a treatment time period which represents a time frame when the magnetic field is generated with DC current.

28. The apparatus of claim 27, wherein the user interface includes a touchscreen display and a plurality of icons representing target treatment locations, wherein the control unit is configured such that based on a selected target treatment location, the control unit calculates a strength of the pulsed magnetic field, an operating frequency and the time period.

29. The apparatus of claim 22, wherein the body is annular shaped, with the target nerve configured to be received in an opening defined thereby, or the body is an elongated flexible band that includes a pair of magnetic field generating elements spaced apart from one another along one surface of the band.

30. The apparatus of claim 29, wherein each of the magnetic field generating elements has a first fastening element and the one surface of the band has a complementary second fastening element that permits each of the magnetic field generating elements to be securely attached to the one surface and be repositionable along the one surface such that a distance between the magnetic field elements is variable.

31. The apparatus of claim 22, wherein the predetermined magnetic field strength is between 10 mT and 25 mT.

32. The apparatus of claim 22, wherein the predetermined frequency is between 0.16 Hz and 0.5 Hz.

33. The apparatus of claim 21 wherein the predetermined magnetic field strength and the predetermined frequency are selected such that the amplitude of the compound action potential of the target nerve increases by at least about 25%.

34. The apparatus of claim 21 wherein the predetermined magnetic field strength and the predetermined frequency are selected such that the amplitude of the compound action potential of the target nerve increases by at least about 50%.

35. The apparatus of claim 21 wherein the predetermined magnetic field strength and the predetermined frequency are selected such that the amplitude of the compound action potential of the target nerve increases by at least about 100%.

36. A method for improving neuronal performance of a target nerve of a patient, comprising:
exposing the target nerve to an effective single pulsed magnetic field generated by DC current having a predetermined magnetic field strength at a predetermined frequency, the pulsed magnetic field, in one cycle time, being the predetermined magnetic field strength for a first predetermined time and substantially zero for a second predetermined time;
selecting the predetermined magnetic field strength and the predetermined frequency such that an amplitude of a compound action potential of the target nerve increases as a result of the exposure and remains elevated for a time period after the exposure has ended; the compound action potential being an electrical signal traveling through the target nerve.

37. The method of claim 36, wherein the amplitude of the compound action potential is increased by at least about 25%.

38. The method of claim 36, wherein the amplitude of the compound action potential is increased by at least about 50%.

39. The method of claim 36, wherein the amplitude of the compound action potential is increased by at least about 100%.

40. The method of claim 36, wherein exposing the nerve comprises: supplying the DC current from a portable DC power source comprising a battery.

41. The method of claim 36, wherein exposing the nerve comprises:
supplying AC current from an AC power source; and
converting the AC current to the DC current using an AC/DC converter.

42. The method of claim 36, wherein the time period is greater than 1 hour.

43. The method of claim 36, wherein the time period is greater than 6 hours.

* * * * *